(12) United States Patent
Shimizu

(10) Patent No.: US 6,241,774 B1
(45) Date of Patent: Jun. 5, 2001

(54) ARTIFICIAL ESOPHAGUS

(75) Inventor: Yasuhiko Shimizu, 39-676, Kohataogurayama, Uji-shi, Kyoto 611-0002 (JP)

(73) Assignees: Yasuhiko Shimizu, Kyoto; Tapic International Co., Ltd., Tokyo, both of (JP)

( * ) Notice: Subject to any disclaimer, the term of this patent is extended or adjusted under 35 U.S.C. 154(b) by 0 days.

(21) Appl. No.: 09/308,556

(22) PCT Filed: Nov. 19, 1997

(86) PCT No.: PCT/JP97/04204

§ 371 Date: May 20, 1999

§ 102(e) Date: May 20, 1999

(87) PCT Pub. No.: WO98/22156

PCT Pub. Date: May 28, 1998

(30) Foreign Application Priority Data

Nov. 20, 1996 (JP) .................................................. 8-308855

(51) Int. Cl.[7] .......................................................... A61F 2/02
(52) U.S. Cl. ............................................................. 623/23.64
(58) Field of Search .............................. 623/23.64, 23.65, 623/23.7, 23.71; 606/151, 152, 153, 154; 435/273, 1.1; 424/423, 422

(56) References Cited

U.S. PATENT DOCUMENTS

| 3,272,304 | | 9/1966 | Artandi et al. . | |
|---|---|---|---|---|
| 4,689,399 | * | 8/1987 | Chu | 530/356 |
| 4,842,575 | | 6/1989 | Hoffman, Jr. et al. | 600/36 |
| 4,948,540 | * | 8/1990 | Nigam | 264/28 |
| 5,026,381 | * | 6/1991 | Li | 623/12 |
| 5,108,424 | | 4/1992 | Hoffman, Jr. et al. | 623/1 |
| 5,387,236 | * | 2/1995 | Noishiki et al. | 623/1 |
| 5,411,887 | * | 5/1995 | Sjolander | 435/273 |
| 5,607,590 | * | 3/1997 | Shimizu | 210/490 |
| 5,733,337 | * | 3/1998 | Carr, Jr. et al. | 623/11 |
| 5,993,844 | * | 11/1999 | Abraham et al. | 424/423 |
| 6,090,996 | * | 7/2000 | Li | 623/11 |

FOREIGN PATENT DOCUMENTS

| 1-110366 | 4/1989 | (JP) . |
|---|---|---|
| 2-109569 | 4/1990 | (JP) . |
| WO 95/25428 | 9/1995 | (WO) . |

OTHER PUBLICATIONS

Yukinobu Takimoto, et al. "Replacement Of Long Segments Of The Esophagus With A Collagen–Silicone Composite Tube", ASAIO JOURNAL, vol. 41, No. 3 Jul. 1, 1995, pp. 605–608.

Copy of Communication dated Nov. 15, 2000 Supplementary European Search Report re corresponding EPA No. 97912505.1–2107–JP9704204, (3) pages.

Derwent Abstract No. 007974402 which relates to Japanese Patent No. 57–115250 (Jul. 17, 1982). (See attached Japanese language copy of said Patent.)

Derwent Abstract No. 004314445 which relates to Japanese Patent No. 60–203264 (Oct. 14, 1985). (See attached Japanese language copy of said Patent.)

* cited by examiner

*Primary Examiner*—David J. Isabella
(74) *Attorney, Agent, or Firm*—David G. Conlin; Robert L. Buchanan; Edwards & Angell, LLP

(57) ABSTRACT

Disclosed is an artificial esophagus suitable for human use that includes a fine fibrous collagen layer and a tubular outer surface. The invention generally provides a degradable artificial structure that helps maintain an existing esophagus or form a new esophagus. The invention has many important uses including improving esophageal reconstruction techniques.

5 Claims, No Drawings

ARTIFICIAL ESOPHAGUS

TECHNICAL FIELD

The present invention relates to an artificial esophagus.

BACKGROUND ART

Although materials of biological origin as well as artificial materials composed of polymer materials and so forth are used as an artificial esophagus for esophagus reconstruction following excision of the esophagus due to esophageal cancer and so forth, an artificial esophagus (Japanese Patent Provisional Publication No. 2-109569) has been reported in which a collagen coating layer is formed on the outer surface of a silicone tube for use as an artificial esophagus that promotes regeneration of esophageal epithelium at the portion where the esophagus is missing to regenerate a new esophagus without any artificial material remaining following esophagus reconstruction. However, since the collagen coating layer in this artificial esophagus swells and softens as a result of coming in contact with humor, suturing is difficult, thereby requiring sophisticated technique by the surgeon. In the case of suturing by a surgeon not having sophisticated technique, there is the risk of hemorrhage and leakage of air from the sutured site, and in the case of applying as a mediastinal esophagus, the postoperative process is not very good and there is the risk of causing death of the patient in which the artificial esophagus is applied.

DISCLOSURE OF INVENTION

With this in mind, there has been a need for the development of an artificial esophagus that is able to maintain for a desired duration the characteristic effect of collagen of promoting regeneration of esophageal epithelium at the portion where the esophagus is missing to regenerate a new esophagus, is degraded and absorbed by the body together with generation of new esophagus without leaving a foreign object in the body, has physical properties (strength) that do not require the surgeon who performs suturing to have a sophisticated technique, prevents hemorrhage and leakage of air from the sutured site, and allows a stent to be easily removed following esophagus reconstruction.

As a result of earnest research to solve the above problems, the inventor of the present invention found that an artificial esophagus having a fine fibrous collagen layer has excellent effects, thereby leading to completion of the present invention.

The present invention is characterized by being an artificial esophagus having a fine fibrous collagen layer on the outer surface of a tube. In addition, the present invention is characterized by being a method for producing said artificial esophagus that includes a step wherein a fine fibrous collagen layer is formed on the outer surface of a tube followed by performing crosslinking treatment.

The artificial esophagus of the present invention is an artificial esophagus having a non-woven fabric-like collagen layer wherein fine fibers composed of collagen molecules are overlapped in multiple layers on the outside of a tube that fulfills the role of a lumen retaining core member. The thickness of this fine fibrous collagen layer is preferably about 2–10 mm, and particularly preferably about 5 mm. In addition, the tube serving as the lumen retaining core member uses a tube composed of, for example, medical silicone sheet (thickness: preferably about 0.5–5 mm, and particularly preferably 1–2 mm). Since the artificial esophagus of the present invention is sutured to the body with a tube serving as a lumen retaining core member, the inner diameter of the tube used is preferably about 15–30 mm, and particularly preferably 20 mm, or can be different depending on the particular case. The length of the tube used can also be different depending on the particular case. Although the artificial esophagus of the present invention has strength that allows suturing to be performed easily even with this artificial esophagus alone, in cases when even higher levels of strength are required, it may also have a collagen membrane layer on at least one side (outside) of the fine fibrous collagen layer. This collagen membrane differs from the fine fibrous collagen layer in that it is a collagen membrane having an amorphous structure in which collagen molecules are dispersed in the form of monomers and oligomers. The collagen which is the raw material of the fine fibrous collagen layer of the artificial esophagus of the present invention may be various types of conventional collagen, and preferably neutral solubilized collagen, acidic solubilized collagen, alkaline solubilized collagen or enzyme solubilized collagen. Alkaline solubilized collagen and enzyme solubilized collagen are the result of treating insoluble collagen with base or enzyme, respectively (examples of which include pepsin, trypsin, chymotrypsin, papain and pronase). As a result of this treatment, the strongly antigenic telopeptide portion of the collagen molecules is removed resulting in decreased antigenicity. Consequently, these types of collagen can be used particularly preferably. There are no particular restrictions on the origin of these collagens, and collagens can typically be used that are obtained by extraction and purification from the skin, bone, cartilage, tendon or organs of animals such as cows, pigs, rabbits, sheep and kangaroos.

In preparing the artificial esophagus of the present invention using the above-mentioned collagen as a raw material, a fine fibrous collagen layer is formed on the outer surface of a tube used as a lumen retaining core member of the artificial esophagus, for example, a tube composed of medical silicone sheet as described above.

The fine fibrous collagen layer can be formed on the outer surface of the tube preferably by the method described below. To begin with, an approximately 1 N hydrochloric acid solution (about pH 3) of extracted and purified collagen as described above (preferably about 0.5–3 wt % and particularly preferably about 1 wt %) is prepared, and the above tube (a rod-shaped core member, for example, a rod of made of Teflon, may be used) is immersed in the collagen hydrochloric acid solution (the lumen of said tube is sealed by inserting a rod-shaped object). By using such a method, a collagen hydrochloric acid solution layer is formed at a uniform thickness on the outer surface of the tube. The thickness of the collagen hydrochloric acid solution layer is preferably about 20–100 mm, and particularly preferably about 50 mm. This is then frozen preferably at about −15° C. to 0° C., and particularly preferably about 0° C., for preferably about 6–24 hours, and particularly preferably about 12 hours. As a result of this freezing, fine fragments of ice are formed between the collagen molecules dispersed in the hydrochloric acid solution, and this causes the collagen hydrochloric acid solution to separate into layers. Fine fibers are then formed as a result of the collagen molecules rearranging. Next, the silicone tube having the above frozen collagen hydrochloric acid solution layer on its outer surface is freeze-dried in a vacuum preferably at about −15° C. to 0° C., and particularly preferably about 0° C., for preferably about 12–48 hours, and particularly preferably about 24 hours. As a result of this freeze-drying, in addition to the fine ice fragments between the collagen molecules vaporizing, the collagen hydrochloric acid solution layer becomes a non-woven fabric-like collagen layer in which fine fibers composed of collagen molecules are overlapped in multiple layers. Moreover, the tube having on its outer surface this fine fibrous collagen layer is uniformly compressed using a pressing apparatus. In the artificial esophagus of the present invention, the thickness of the fine fibrous collagen layer after compression is preferably about 2–10 mm, and particularly preferably about 5 mm. Thus, the compression ratio, which is the ratio of the thickness of the collagen layer after compression to the thickness before compression, is preferably about 0.05–0.3, and particularly preferably about 0.1.

Next, the tube on which is formed on its outer surface the above fine fibrous collagen layer is subjected to crosslinking treatment. As a result of performing this crosslinking treatment, the artificial esophagus of the present invention is adjusted so as to remain in the body for a desired duration after application. Although examples of crosslinking methods include those using gamma rays, electron beam, ultraviolet rays, glutaraldehyde and epoxy, as well as thermal dehydration crosslinking using heat, it is preferable to perform thermal dehydration crosslinking since it allows the degree of crosslinking to be easily controlled and there are no problems of a crosslinking agent having an effect on the body. In order to perform thermal dehydration crosslinking, the tube on which is formed the collagen layer obtained above is heated in a vacuum preferably at about 105–150° C., and particularly preferably 120–150° C., for preferably about 6–24 hours, and particularly preferably 6–12 hours. If heated at less than 105° C., a sufficient crosslinking reaction does not occur. On the other hand, if heating exceeds 150° C., the collagen ends up denaturing. Furthermore, in the case of using a core member instead of a tube, said core member should be removed from the tube after crosslinking, and a silicone tube should be inserted into said tube lumen.

Although the artificial esophagus of the present invention characterized by having a fine fibrous collagen layer on the outer surface of a tube has strength that allows suturing to be performed easily even with this artificial esophagus alone, in cases when even higher levels of strength are required, a collagen membrane having an amorphous structure as described above may be additionally formed on at least one side (outside) of the fine fibrous collagen layer. An artificial esophagus having a fine fibrous collagen layer on which is formed a collagen membrane on its outside can be produced in the manner described below.

A collagen hydrochloric acid solution layer of uniform thickness is formed and dried (the formation of this collagen solution layer and drying procedure is repeated several times, and preferably about 10 times) using an about 1 N hydrochloric acid solution (pH of about 3) of extracted and purified collagen prepared in the same manner as described above (collagen concentration is preferably about 0.5–3 wt %, and particularly preferably about 1 wt %) on the outer surface of a tube (a core member may also be used as previously described) on which is formed on its outer surface a fine fibrous collagen layer prepared with the above-mentioned method. The thickness of the collagen hydrochloric acid solution layer is preferably about 5–20 mm, and particularly preferably about 5–10 mm, overall. Finally, a layer of a collagen membrane having an amorphous structure in which collagen molecules are dispersed is formed on the outside of said fine fibrous collagen layer. Furthermore, the previously mentioned thermal dehydration crosslinking is performed in this state. In addition, in the case of using a core member, said core member and silicone tube are exchanged in the same manner as previously mentioned, namely after crosslinking being performed. In addition, in the case of an artificial esophagus in which a layer of collagen membrane having an amorphous structure is formed on both sides of said fine fibrous collagen layer, a rod-shaped core member is used in place of the silicone tube during formation of the fine fibrous collagen layer to first produce a tube composed only of fine fibrous collagen, after which a method is employed in which said tube is immersed in a similar collagen hydrochloric acid solution as described above to form a collagen hydrochloric acid solution layer of uniform thickness on the inside and outside of the fine fibrous collagen layer followed by drying (the formation of the collagen solution layer and drying procedure are repeated several times in the same manner as previously described). In this case as well, the thickness of the collagen hydrochloric acid solution layer that is formed is the same as the case of forming on the outside only. In addition, thermal dehydration crosslinking is also performed in this state. Finally, said core member is removed and a silicone tube is inserted into a tube of fine fibrous collagen having a collagen membrane with an amorphous structure on both sides.

As described above, by forming a layer of collagen membrane on at least the outside of a fine fibrous collagen layer, in addition to such a frayed state as observed in the non-woven fabric-like material on the surface of the fine fibrous collagen layer being covered by the amorphous structure collagen membrane, a portion of said amorphous structure collagen penetrates into said fine fibrous collagen layer, thereby further improving the physical properties of the artificial esophagus of the present invention and additionally improving suturing and retention in the body.

Furthermore, it is preferable to have a trace amount of b-FGF (fibroblast growth factor) in the fine fibrous collagen layer and/or amorphous structure collagen membrane layer. In addition to enhancing the speed at which new esophagus is regenerated, an esophagus is regenerated that has a tissue structure that is more normal. Furthermore, an example of a method for making b-FGF contain, gelatin hydrogel microspheres containing b-FGF dissolved in PBS (phosphate buffered saline) may be injected into said layers with a syringe either immediately before application in the body or immediately after suturing to body tissue.

BEST MODE FOR CARRYING OUT THE INVENTION

EXAMPLES

As a result of immersing a Teflon rod having a length of about 9 cm and diameter of about 22 mm in a 1 N hydrochloric acid solution containing about 1 wt % enzyme solubilized collagen originating in pig skin and then lifting out said rod, a collagen hydrochloric acid solution layer was formed at a thickness of about 50 mm on the surface of the Teflon rod, after which this was frozen at about 0° C. for about 12 hours. This was then freeze-dried in a vacuum at about 0° C. for about 24 hours to form a fine fibrous collagen layer from the collagen hydrochloric acid solution layer. The Teflon rod on which was formed on its surface a fine fibrous collagen layer was compressed by using a pressing apparatus so that the thickness of the fine fibrous collagen layer was reduced to about 5 mm. Next, the Teflon rod having the compressed fine fibrous collagen layer on its surface was again immersed in the previous collagen hydrochloric acid solution to form a collagen hydrochloric acid solution layer on the outer surface of the fine fibrous collagen layer followed by airdrying. This set of immersing in collagen hydrochloric acid solution and airdrying was repeated 10 times, and a layer of collagen membrane having an amorphous structure was formed at a thickness of 0.5 mm on the outer surface of the fine fibrous collagen layer. Further, the Teflon rod having both collagen layers on its outer surface was heated at 105° C. for 12 hours in a vacuum to perform thermal hydration crosslinking treatment on said collagen layer. The Teflon rod was then removed, and a silicone tube having a length of about 9 cm, inner diameter of about 20 mm and thickness of about 1 mm was inserted into the lumen of the tube composed of both collagen layers to obtain the artificial esophagus of the present invention.

A 5 cm portion in the thoracic part of esophagus of a beagle dog was replaced with the artificial esophagus of the present invention.

Furthermore, immediately before applying the artificial esophagus of the present invention, 280 mg of gelatin hydrogel microspheres containing 100 μg of b-FGF dissolved in 1 ml of PBS were injected into the collagen layer.

As a result of observing said replaced site one month after surgery, normal esophagus tissue was confirmed to be reconstructed at said replaced site.

In a conventional artificial esophagus, 2–3 months are required for its reconstruction, and moreover, the patient in which the artificial esophagus is applied has the risk of dying prior to reconstruction depending on the skill with which the suturing procedure is performed in the replacement surgery. In comparison, the artificial esophagus of the present invention was confirmed to be significantly superior in this respect.

In comparison with an artificial esophagus of the prior art, since the artificial esophagus of the present invention has excellent physical properties, and particularly excellent suturing, it does not require sophisticated technique on the part of the surgeon performing suturing. Consequently, there is hardly any occurrence of leakage of air or hemorrhage from the sutured site caused by a lack of suturing technical skill on the part of the surgeon. In addition, the collagen layer does not immediately dissolve, but continues to retain its shape for a desired duration, while promoting regeneration and epithelial formation of esophagus tissue. Correspondingly, body cells penetrate into the collagen layer and grow by using the collagen layer as a foothold thereby resulting in esophagus regeneration and replacement of the collagen layer that is gradually broken down and absorbed. Finally, the artificial esophagus applied in the body disappears and the biological esophagus is completely regenerated (an esophagus is reconstructed having a normal tissue structure). Consequently, the tube that has completed its role as a lumen retaining core member can be easily removed following esophagus reconstruction.

INDUSTRIAL APPLICABILITY

The artificial esophagus of the present invention can be preferably used since it retains the characteristic effect of collagen of promoting regeneration of esophageal epithelium at the portion where the esophagus is missing to regenerate a new esophagus, is degraded and absorbed by the body together with regeneration of new esophagus without leaving a foreign object in the body, has adequate strength by itself to withstand suturing to eliminate the occurrence of hemorrhage and leakage of air from the sutured site caused by the skill of the suturing technique of the surgeon, and allows a stent to be easily removed following esophagus reconstruction.

What is claimed is:

1. An artificial esophagus comprising:
    a tube which fulfills the role of a lumen retaining core member;
    a non-woven fabric-like collagen layer on the outer surface of the tube, wherein fine fibers composed of collagen molecules are overlapped in multiple layers, the collagen layer being obtained by freezing a hydrochloric acid solution of extracted collagen followed by freeze-drying; and an amorphous collagen layer on at least the outer surface of said non-woven fabric like collagen layer.

2. The artificial esophagus according to claim 1, wherein b-FGF as growth factor is incorporated into the non-woven fabric-like collagen layer.

3. A method for producing the artificial esophagus according to claim 1 comprising the following steps:
    forming a layer of hydrochloric acid solution extracted collagen on the outer surface of the tube;
    freezing said layer of extracted collagen;
    freeze-drying said frozen layer of extracted collagen to obtain a fine fibrous collagen layer;
    compressing said fine fibrous collagen layer;
    forming a layer of hydrochloric acid solution extracted collagen at least on the outer surface of said fine fibrous collagen layer to obtain an amorphous collagen layer; and
    performing thermal dehydration crosslinking treatment to the resulting tube having two layers composed of collagen on the outer surface thereof to produce the artificial esophagus.

4. The artificial esophagus of claims 1 or 2, wherein the tube and the non-woven fabric-like collagen layer are contiguous.

5. The method of claim 3, wherein the tube and the fine fibrous collagen layer are contiguous.

* * * * *